(12) United States Patent
Lochhead et al.

(10) Patent No.: US 9,341,504 B2
(45) Date of Patent: May 17, 2016

(54) FLUIDIC ASSAY CARTRIDGE WITH CONTROLLED PASSIVE FLOW

(75) Inventors: Michael J. Lochhead, Boulder, CO (US); Kurt R. Vogel, Boulder, CO (US); Keagan B. Rowley, Boulder, CO (US)

(73) Assignee: MBio Diagnostics, Inc., Boulder, CO (US)

( * ) Notice: Subject to any disclaimer, the term of this patent is extended or adjusted under 35 U.S.C. 154(b) by 476 days.

(21) Appl. No.: 13/878,611

(22) PCT Filed: Oct. 11, 2011

(86) PCT No.: PCT/US2011/055844
§ 371 (c)(1),
(2), (4) Date: Jun. 24, 2013

(87) PCT Pub. No.: WO2012/051218
PCT Pub. Date: Apr. 19, 2012

(65) Prior Publication Data
US 2013/0283931 A1    Oct. 31, 2013

Related U.S. Application Data

(60) Provisional application No. 61/391,911, filed on Oct. 11, 2010.

(51) Int. Cl.
*G01N 21/03* (2006.01)
*G01N 21/05* (2006.01)
(Continued)

(52) U.S. Cl.
CPC ............... *G01F 1/34* (2013.01); *B01L 3/50273* (2013.01); *B01L 3/502723* (2013.01);
(Continued)

(58) Field of Classification Search
CPC ............... B01L 2300/0864; B01L 2200/0605; B01L 2300/069; B01L 2300/0816; B01L 2300/087; B01L 2400/0406; B01L 3/50273; B01L 3/502746; B01L 2200/0621; B01L 2200/0642; B01L 2200/0684; B01L 2300/0803
USPC ......... 422/400; 356/128; 385/12, 15, 33, 129, 385/141; 435/30, 288.5; 506/9–22
See application file for complete search history.

(56) References Cited

U.S. PATENT DOCUMENTS 8,300,993 B2 * 10/2012 Moll .................... G01N 21/552
        385/14
8,586,347 B2 * 11/2013 Lochhead .......... G01N 21/6452
        385/14

(Continued)

FOREIGN PATENT DOCUMENTS

FR    WO 2012048096 A2 *  4/2012 ............ B01L 3/5025

OTHER PUBLICATIONS

PCT/US2011/055844 International Search Report and Written Opinion mailed Jun. 12, 2012, 19 pages.
(Continued)

*Primary Examiner* — Hezron E Williams
*Assistant Examiner* — Gedeon M Kidanu
(74) *Attorney, Agent, or Firm* — Lathrop & Gage LLP (57) ABSTRACT

A fluidic cartridge (110) with passively driven fluid flow is disclosed. The disclosed device and method solve problems associated with passive-flow fluidics by using a wicking pad (510) and/or a tilting means to prevent channel draining and backflow. The disclosure further provides means for adding liquid to the cartridge in multiple steps, without requiring liquid aspiration or removal.

19 Claims, 8 Drawing Sheets

(51) Int. Cl.
*G01F 1/74* (2006.01)
*G01F 1/34* (2006.01)
*B01L 3/00* (2006.01)

(52) U.S. Cl.
CPC .......... *G01F 1/74* (2013.01); *B01L 2200/0642* (2013.01); *B01L 2300/069* (2013.01); *B01L 2300/0825* (2013.01); *B01L 2300/0887* (2013.01); *B01L 2400/0406* (2013.01); *B01L 2400/0457* (2013.01); *B01L 2400/0688* (2013.01); *G01N 2021/0346* (2013.01); *G01N 2021/056* (2013.01)

(56) References Cited

U.S. PATENT DOCUMENTS

| | | | | |
|---|---|---|---|---|
| 8,753,894 | B2* | 6/2014 | Tondra | G01R 33/12 422/68.1 |
| 2002/0094147 | A1* | 7/2002 | Herron | G01N 21/0303 385/12 |
| 2005/0048597 | A1* | 3/2005 | Smith | B01L 3/5025 435/30 |
| 2005/0249641 | A1 | 11/2005 | Blankenstein et al. | |
| 2006/0078986 | A1 | 4/2006 | Ly et al. | |
| 2007/0297949 | A1* | 12/2007 | Wu | B01L 3/502753 422/400 |
| 2009/0305231 | A1* | 12/2009 | Weidemaier | B82Y 5/00 435/5 |
| 2010/0159611 | A1* | 6/2010 | Song | A61B 10/007 436/163 |
| 2010/0220318 | A1* | 9/2010 | Moll | G01N 21/552 356/128 |
| 2011/0065209 | A1* | 3/2011 | Heil | G01N 33/54326 436/501 |
| 2012/0071342 | A1* | 3/2012 | Lochhead | G01N 21/6452 506/9 |
| 2012/0088230 | A1* | 4/2012 | Givens | G01N 21/0303 435/5 |
| 2013/0244313 | A1* | 9/2013 | Dunn | G01N 33/56972 435/287.2 |

OTHER PUBLICATIONS

PCT/US2011/055844 Response to Written Opinion filed Sep. 12, 2012, 12 pages.
PCT/US2011/055844 Written Opinion of the International Preliminary Examining Authority mailed Nov. 26, 2012, 5 pages.
PCT/US2011/055844 International Preliminary Report on Patentability mailed Feb. 27, 2013, 23 pages.
EP Application No. 11 776 948.9 Communication pursuant to 94(3) EPC mailed Aug. 18, 2015, 4 pages.
EP Application No. 11 776 948.9 Response to Communication pursuant to 94(3) EPC, filed Nov. 11, 2015, 9pages.

* cited by examiner

FLUIDIC ASSAY CARTRIDGE WITH CONTROLLED PASSIVE FLOW

RELATED APPLICATIONS

This application claims priority to U.S. Provisional Patent Application No. 61/391,911, filed Oct. 11, 2010, and entitled "Fluidic Assay Cartridge with Controlled Passive Flow." The aforementioned application is incorporated by reference into the present application in its entirety and for all purposes.

GOVERNMENT INTEREST

This invention was made with government support under award number AI068543 awarded by the National Institute of Health. The Government has certain rights in the invention.

BACKGROUND

The present disclosure pertains to methods for regulating fluidic flow in a device. In particular, the disclosure pertains to devices and methods for performing liquid-based assays in fluidic cartridges, such as those that require multiple liquid steps.

SUMMARY

The disclosed device and method advance the art by providing simple fluidic cartridges that solve problems in the field. The disclosure particularly pertains to fluidic devices with passively driven fluid flow, that is, fluid flow driven by forces such as capillary action and head pressures rather than by active pumping mechanisms. This disclosure also solves some of the problems associated with passive-flow fluidics, namely, channel draining and backflow, among others. The disclosure further provides means for adding liquid to cartridges in multiple steps, without requiring liquid aspiration or removal.

In one embodiment, a device is provided for analyzing or processing a liquid sample. The device may contain a first substrate, a second substrate, a fluidic channel, an inlet port and an outlet port. The first substrate may have a first inner surface and a first outer surface. Similarly, the second substrate may have a second inner surface and a second outer surface. The fluidic channel may be partly defined by the first inner surface of the first substrate and the second inner surface of the second substrate. In another aspect, the first substrate may form, at least in part, the lower wall of the fluidic channel, while the second substrate may form, at least in part, the upper wall of the fluidic channel.

In one embodiment, the fluidic channel is connected directly or indirectly to the inlet port on one end and to the outlet port on the other end. In another embodiment, a wicking pad may be placed on the second substrate, wherein said wicking pad is positioned at a distance from said outlet port. For instance, the wicking pad may be attached to the second outer surface of the second substrate. In one aspect, the wicking pad is positioned at a certain distance (or gap) from the outlet port, wherein the distance may help prevent the wicking pad from draining the fluidic channel. In another embodiment, the wicking pad may also prevent liquid that has already made contact with the wicking pad from flowing back into the outlet port. In one aspect, the distance or gap is between 1 and 5 mm. In another aspect, the distance or gap is between 2 and 4 mm.

In another embodiment, the device, such as a fluidic cartridge, may be designed such that the flow of the liquid sample through the fluidic channel is driven by a pressure differential between the inlet port and the outlet port. In another embodiment, when added to the inlet port, the liquid sample may form an inlet reservoir with a depth of $H_1$. As the liquid flows through the channel and reaches the outlet port, it may form an outlet reservoir having a depth of $H_2$. For purpose of this disclosure, $H_1$, and $H_2$ may be both from about 1 to about 10 mm. In another embodiment, when $H_1$, is greater than $H_2$, a pressure differential is created between the inlet and outlet ports.

In another embodiment, the inlet port may have physical dimensions that provide an inlet liquid volume reservoir that feeds the fluidic channel. In one aspect, the inlet port may have a cylindrical geometry with diameter in the range of about 1 to 10 mm and a height of about 1 to 10 mm. In another aspect, the inlet port may have a non-cylindrical geometry, such as square, rectangular, or oval shape. In one example, the inlet port may hold about 0.003 to 3 milliliters of liquid.

In another embodiment, the outlet port may be an opening in the solid material defining the fluidic channel. In one aspect, the opening may be circular with a diameter of from about 1 to 5 mm. In another aspect, the opening may be D-shaped, square, rectangular, or oval shape.

Figure 5:
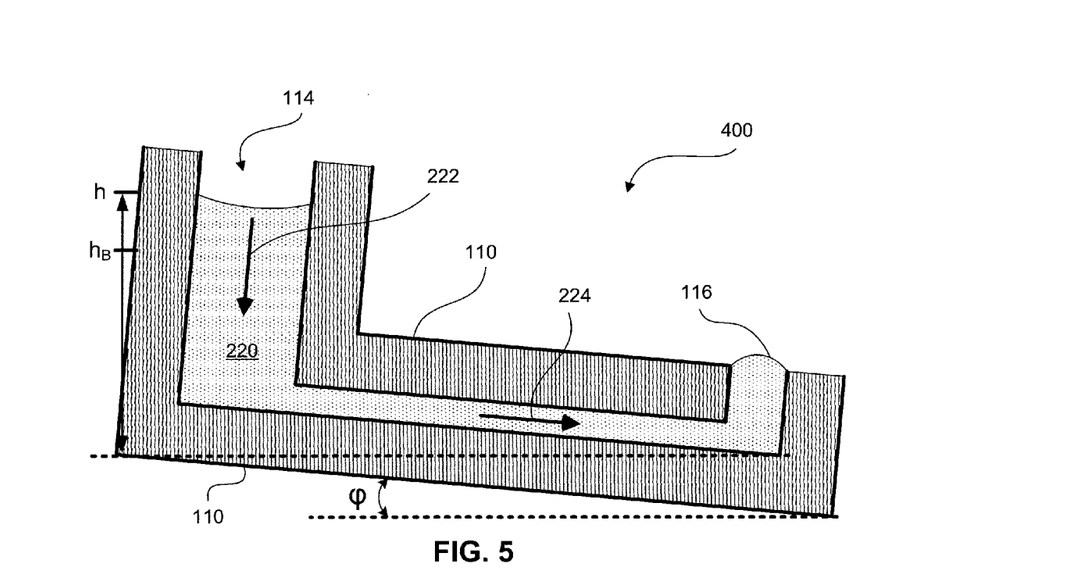
FIG. 5 shows the fluidic cartridge of FIG. 2, this time including a tilt for altering the pressure differential between the inlet port and the outlet port.

In another embodiment, the sample in the inlet port may have a top liquid surface at a height of h relative to the outlet port, wherein the height is defined relative to a level orientation (or horizontal level) even when the device is tilted relative to the level orientation, as shown in FIG. 5.

In another embodiment, the device may be designed with an internal tilt relative to level, such that the height h may drive flow from the inlet port towards the outlet port. In another aspect, the height, h, may be achieved by placing the device in a rack with a pre-determined tilt angle. In one embodiment, the tilt may be at an angle between 2 and 45 degrees relative to a level orientation. In another embodiment, the tilt may be at an angle between 5 and 8 degrees relative to a level orientation.

In another embodiment, the wicking pad is characterized by an absorbance rate and gap between the pad and the outlet port is characterized by a surface energy, wherein the characteristic absorbance rate is selected such that when the absorbance rate exceeds the rate at which liquid emerges from the outlet port, liquid surface tension breaks the liquid connection between the wicking pad and the outlet port, preventing further liquid flow from the outlet port to the wicking pad. In another aspect, the wicking pad may be made of materials having a wicking rate of between 10 and 200 seconds per 4 cm of wick material. By way of example, wicking pad materials may include but are not limited to Whatman 900, Whatman 470, Millipore C182, Millipore C083, and Ahlstrom 222. According to manufacturer's specification, Whatman 900 has a wicking rate of 34 seconds per 4 cm, with 204 mg per sq. cm water absorption, and Whatman 470 has a wicking rate of 77 seconds per 4 cm, with 78 mg per sq. cm water absorption.

In another embodiment, the liquid flow in the fluidic channel may be restored by adding liquid to the inlet port, providing a means for performing multiple liquid additions without requiring aspiration or the removal of liquid from previous additions.

In another embodiment, the fluidic cartridge may contain a rail structure between the outlet port and the wicking pad for directing capillary flow from the outlet port to the wicking pad.

In another embodiment, the first substrate may contain a planar waveguide, and a refractive volume for optically coupling light beams to the planar waveguide. In another aspect, the refractive volume may be integrally formed from the

For purposes of illustrative clarity, certain elements in the drawings may not be drawn to scale.

DETAILED DESCRIPTION

A method and device for reliably performing passive continuous flow in a fluidic channel is described. The method and device: (1) rely on gravity to provide driving pressure; (2) are capable of starting and stopping liquid flow in a controlled manner; and (3) can deliver known quantities of liquid into the channel. The embodiments described herein further provide continuous flow of a known liquid volume through a channel, with flow terminating before the channel is completely drained of liquid. As disclosed herein, this effect may achieved by the following process, beginning with filling an inlet port with a known volume. Pressure-driven flow due to gravity and surface tension moves the liquid through a channel to an outlet port. Introduction of a wicking pad located near the outlet port absorbs the liquid and ensures that flow continues until all the liquid in the inlet port has flowed through the channel. Proper separation of the wicking pad from the outlet port, design of outlet port geometry, and control of solid-liquid-gas surface tension ensures that flow terminates before the channel is drained of liquid. The wicking pad further prevents backflow of liquid through the outlet port into the channel The term "surface tension" is used herein in relation to the surface energies of the solid-liquid, liquid-gas, and solid-gas interfaces associated with the fluidic cartridge. Surface tension or surface energy impacts the ability of a liquid to wet a solid surface, characterized by a liquid-solid-gas interface. In the present invention, exemplary solids include plastics and plastics with modified surface properties. Exemplary liquids include aqueous solutions, including aqueous solutions with surface tensions modified by surface active components such as surfactants or amphiphilic molecules. An exemplary gas is air.

Figure 1:
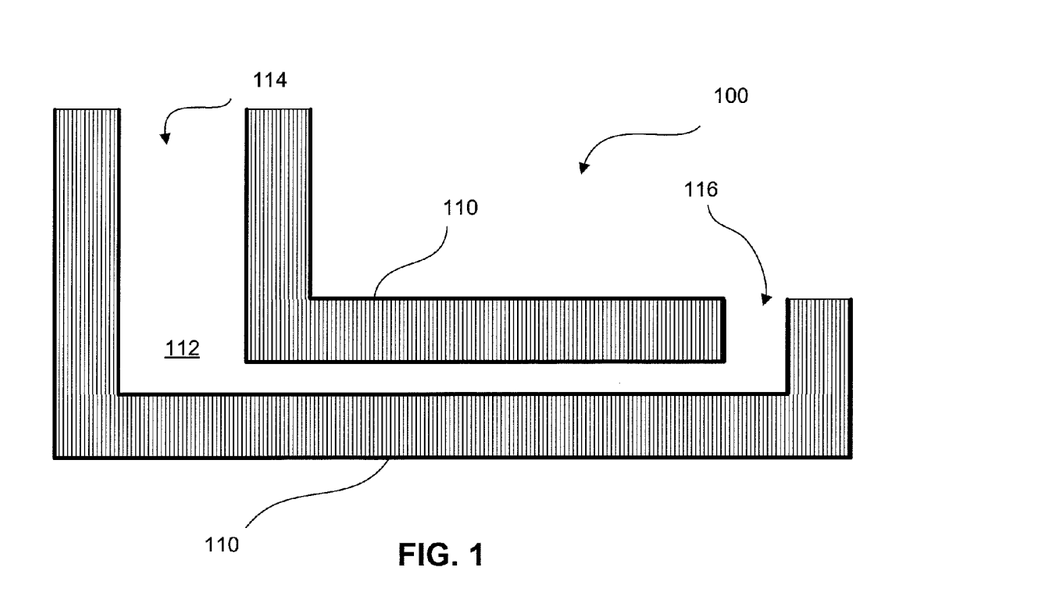
FIG. 1 is a cross-sectional view of a fluidic cartridge, in accordance with an embodiment.

FIG. 1 shows a cross-sectional view of a fluidic cartridge 100, in accordance with an embodiment. Fluidic cartridge 100 includes a casing 110 defining a channel 112 with an inlet port 114 and an outlet port 116. Casing 110 may be formed as a single piece or separate pieces that cooperate to define channel 112, inlet port 114 and outlet port 116. For example, casing 110 may be formed by an injection molding process. As an alternative, casing 110 may be formed from a combination of a lower substrate, defining the bottom of channel 112 and an upper component defining inlet port 114 and top of channel 112 connecting inlet port 114 with outlet port 116.

Figure 2:
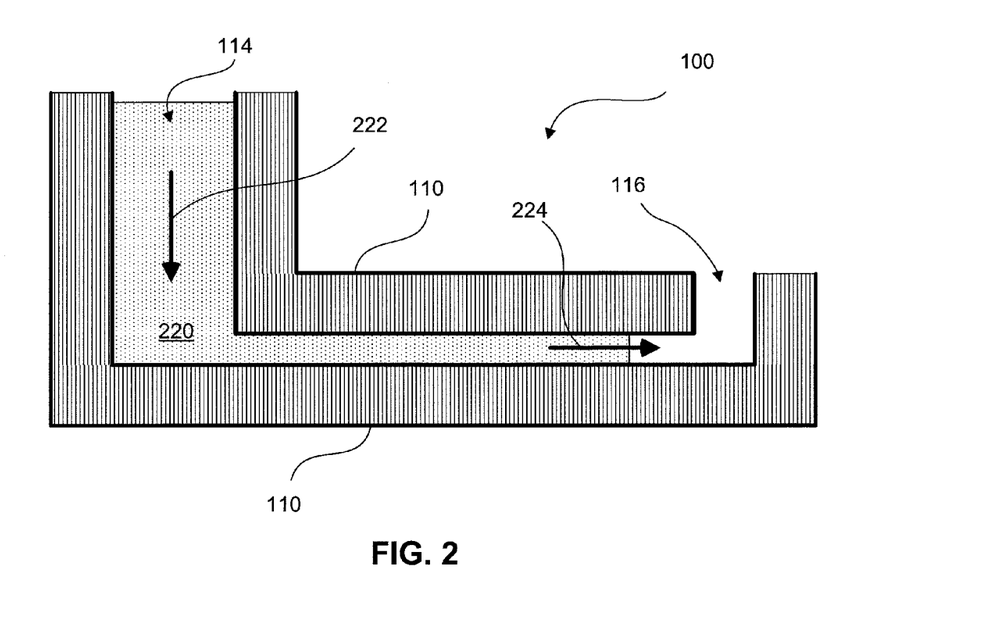
FIG. 2 shows the fluidic cartridge of FIG. 1, illustrating liquid flow into the fluidic cartridge.

For applications, such as in-vitro diagnostics, a liquid 220 (such as an aqueous solution) may be introduced into channel 112 at inlet port 114 of fluidic cartridge 100, as shown in FIG. 2. Due to characteristics such as height differences in the fluidic columns between inlet port 114 and outlet port 116, a differential pressure exists therebetween that drives liquid 220 to flow from inlet port 114 to outlet port 116 in a direction indicated by arrows 222 and 224. If channel 112 has not previously been filled with liquid, capillary forces due to surface tension may also contribute to moving liquid 220 through channel 112.

Figure 3:
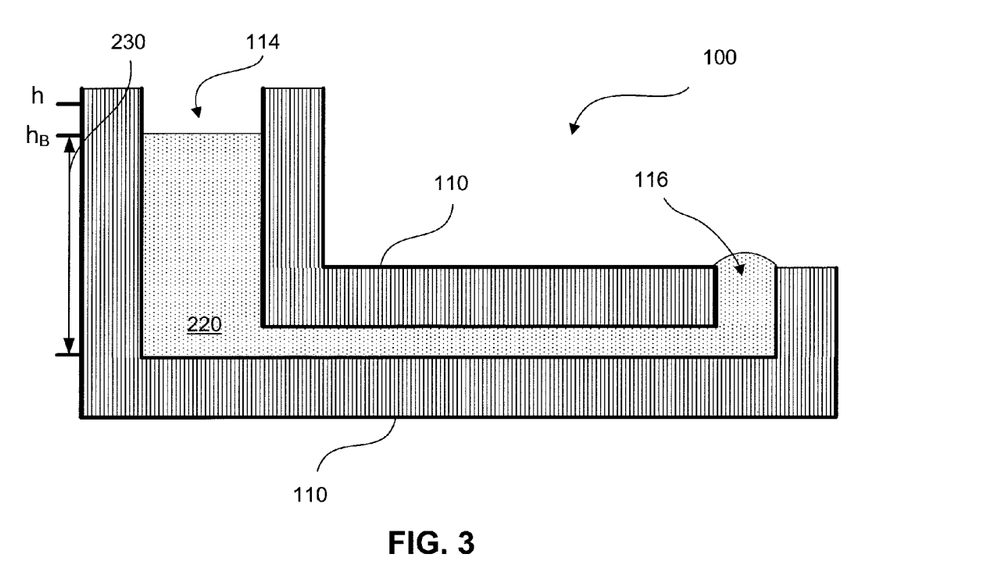
FIG. 3 shows the fluidic cartridge of FIGS. 1 and 2 at the point where the outlet port capillary valve stops liquid flow.

Depending on outlet port 116 geometry (e.g., diameter and shape) and surface tension associated with the liquid, solid cartridge material, and gas (typically air), outlet port 116 can act as a capillary valve with a characteristic burst pressure. Referring to FIG. 3, liquid 220 flows through the channel then stops at a height $h_B$ 230 as determined by the capillary valve burst pressure at outlet port 116.

Figure 4:
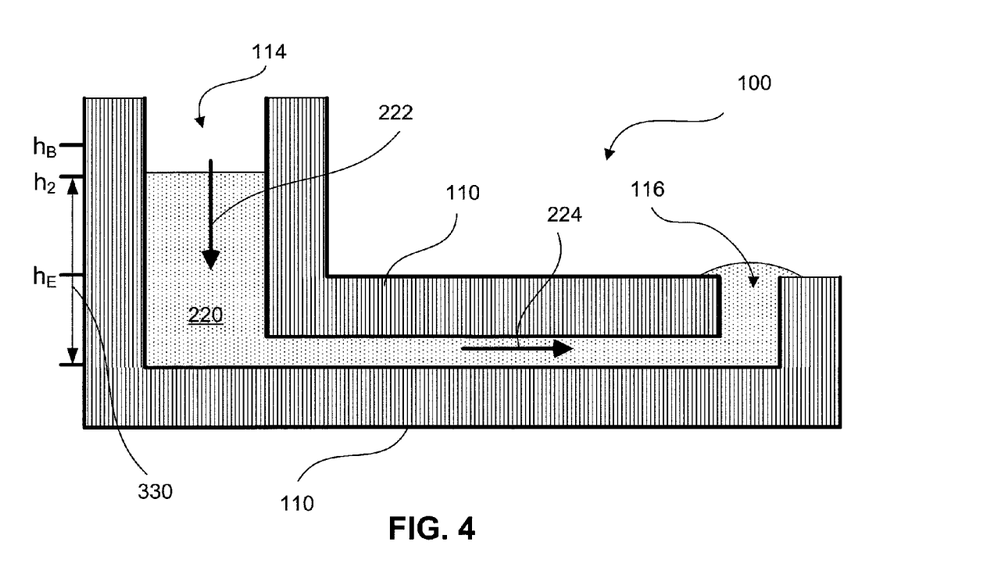
FIG. 4 shows the fluidic cartridge of FIGS. 1 and 2, shown here after the surface tension at the outlet port has been broken as the pressure at the outlet port has exceeded burst pressure.

Once surface tension at outlet port 116 is overcome by the pressure exerted by liquid 220 at outlet 116, liquid 220 begins to flow out of outlet port 116, as shown in FIG. 4. That is, the difference between the fluid pressure and ambient pressure exceeds a burst pressure, overcoming the surface tension at outlet port 116. Consequently, liquid flows continuously through channel 112 until the level of liquid 220 at inlet port 114 drops to equilibrium level $h_E$ 330 (indicated by double arrows), which is lower than first level 230. At this point, flow ceases because the pressures due to surface tension forces and gravity are balanced between inlet port 114 and outlet port 116. For the small dimensional sizes of channel 112 in applications of interest (e.g., on the order of millimeters to tens of millimeters), the gravity-induced forces are comparable in magnitude to surface tension forces.

In one embodiment, a tilt may be introduced to the fluidic cartridge so as to alter the pressure differential between the inlet port and the outlet port. As shown in FIG. 5, a tilted cartridge 400 includes components similar to those of previously-described fluidic cartridge 100. In contrast to the embodiment illustrated in FIGS. 1-3, tilted cartridge 400 is tilted from a level orientation by an angle $\phi$ such that the pressure differential at outlet port 116 is greater than those shown in FIGS. 2 and 3. In effect, the column height of inlet port 114 is increased without requiring additional liquid volume, and thus the gravity-induced pressure is increased over that of the level orientation. As a result, burst pressure is more easily attained, and liquid 220 empties to a relatively lower liquid level in tilted cartridge 400 as compared to level, fluidic cat ridge 100.

Figure 6:
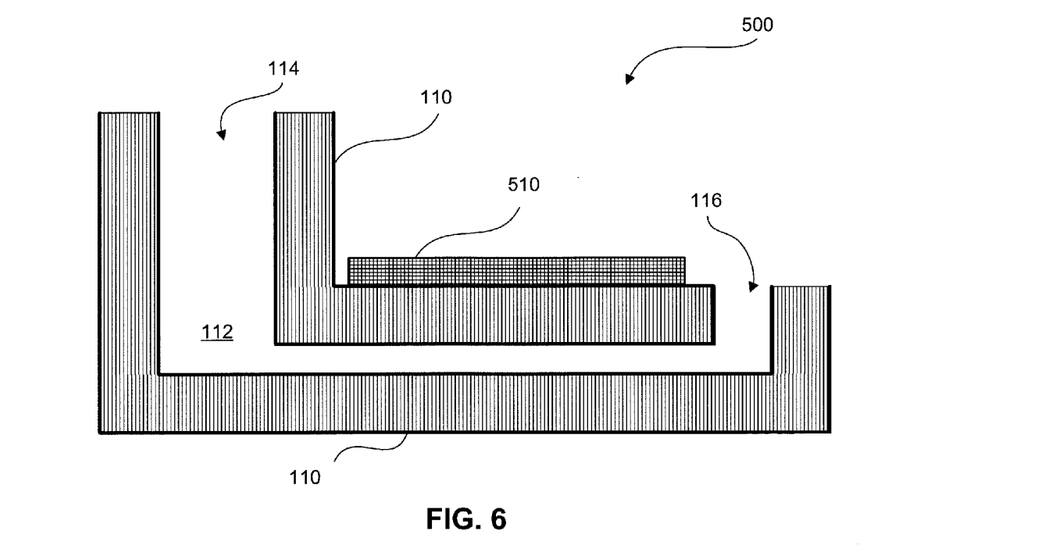
FIG. 6 is a cross-sectional view of a fluidic cartridge including a wicking pad, in accordance with an embodiment.

Regardless of the specific configuration used (e.g., level cartridge 100 or tilted cartridge 400), a fluidic column builds up at outlet port 116 such that at some point liquid flow stops when the pressure at the outlet port balances the pressure at the inlet port. This condition does not always guarantee that all of the liquid in the inlet port 114 flows through channel 112 to outlet port 116. One way to maintain liquid flow through channel 112 is to introduce a wicking pad, which essentially acts as a reservoir for absorbing liquid therein. As will be explained below, the wicking pad acts to reduce the column height of the outlet port such that liquid flow is maintained. FIG. 6 is a cross-sectional view of a fluidic cartridge 100 including a wicking pad 510, in accordance with an embodiment.

Figure 7:
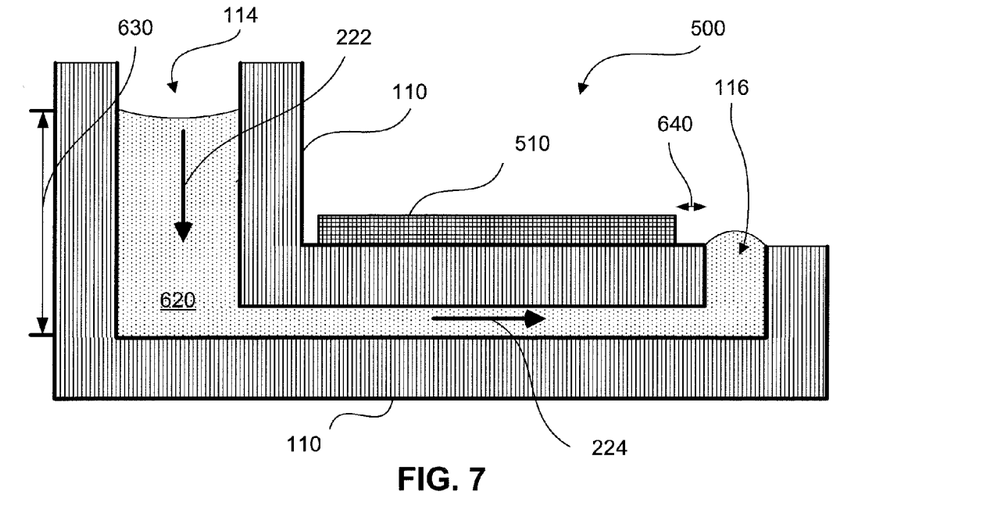
FIG. 7 shows the fluidic cartridge of FIG. 6, illustrating the liquid flow in the fluidic cartridge with the wicking pad.
Figure 8:
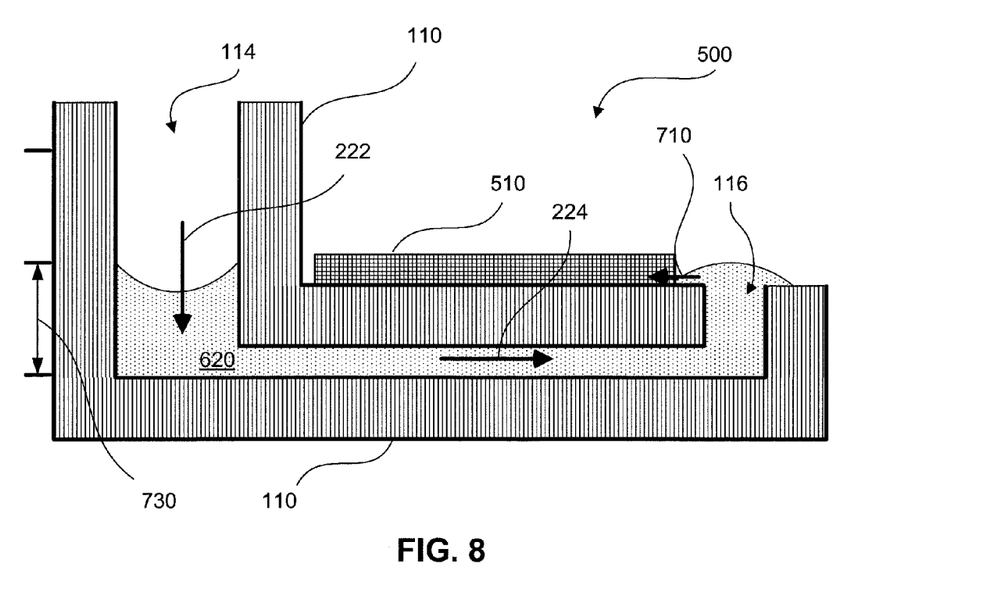
FIG. 8 shows the fluidic cartridge of FIGS. 6 and 7, shown here after the surface tension at the outlet port has been broken as the pressure at the outlet port has exceeded burst pressure such that the liquid, upon contacting the wicking pad, is absorbed into the wicking pad.

As shown in FIG. 7, liquid 620 may be inserted into fluidic cartridge 500 such that, at inlet port 114, liquid 620 reaches a level 630 while liquid 620 is kept within outlet port 116 by surface tension. When the burst pressure is exceeded, as shown in FIG. 8, the liquid flows out from outlet 116 in a manner dependent on the liquid-solid-gas surface tension and solid surface geometry. As the liquid column at outlet 116 expands, it eventually makes contact with wicking pad 510, which quickly absorbs the liquid. The strong capillary forces of the wicking pad absorb liquid at a rate faster than the rate at which channel 224 can supply liquid to outlet port 116. Due to this rate difference, the liquid column height at outlet 116 is rapidly decreased. After absorption by the wicking pad, the liquid column height at outlet 116 is decreased and then subsequently replenished by flow through channel 112. Provided that the column height of inlet 114 provides enough pressure for the liquid to repeatedly overcome the burst pressure and re-contact the wicking pad, back pressure from the liquid column of outlet 116 is avoided and continuous flow occurs in channel 112. Flow through channel 112 is maintained until the liquid column height of inlet 114 drops such that there is insufficient pressure to overcome the burst pressure of outlet 116. Careful choice of material surface energies, tilt angle, and liquid column heights enables the entire volume of liquid in inlet 114 to be completely emptied through channel 112. In this manner, prescribed amounts of liquid can be flowed from inlet port 114 through channel 112, despite large surface tensions from dimensionally small fluidics geometries that might be encountered in a diagnostic device.

Many applications require that the liquid remain in the channel at all times during liquid flow and after the inlet has emptied. For instance, an in-vitro diagnostic may require the biological sample in the liquid to incubate in the channel for a period of time so as to allow the sample to chemically react with reagents that are immobilized to the channel surface. Capillary pressures obtained by wicking pad 510 can be large enough to pull liquid from channel 112 in an unrestrained or uncontrollable manner, causing the channel to go dry or be filled with detrimental gas bubbles. Liquid flow from the outlet port to the wicking pad is affected by a number of factors: absorbance properties of wicking pad (determined by material composition), geometrical placement of wicking pad with respect to outlet 116, the physical geometry of cartridge features like outlet and inlet ports, and the surface energies of cartridge materials and liquids (determined by material composition, surface treatments, and time-dependent surface adsorption). One or more of these properties can be optimized for desired performance. For instance, surface energies around the outlet port can be modified by plasma treatment to promote wetting of the solid material by the liquid.

In an embodiment, a small gap 640 is introduced between wicking pad 510 and outlet port 116 to prevent draining of channel 112 (see FIG. 7). When the rate of liquid from the outlet port is less than absorbance rate of the wicking pad (such as happens when the inlet port empties), surface tension forces in gap 640 around the outlet port "break" the liquid flow to the wicking pad. To restore flow, the inlet can be filled with sufficient liquid so that once again the inlet pressure exceeds the burst pressure. Flow then resumes as the wicking pad once again absorbs excess liquid from the outlet port. In this manner, flow can be started and stopped multiple times in a controlled manner without draining the channel completely of liquid. A key aspect of the embodiment is that the wicking pad does not actively pump liquid through the channel, but only acts a reservoir to store excess liquids. Gravity provides pressure-driven flow through the cartridge channel.

Figure 9:
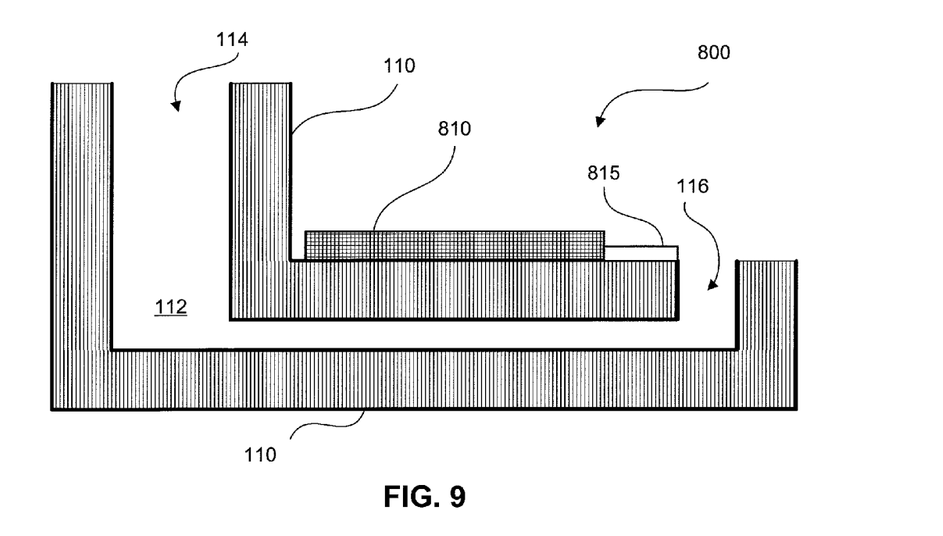
FIG. 9 is a cross-sectional view of a fluidic cartridge including a combination of a wicking pad and a rail, in accordance with an embodiment.

An embodiment also employs the use of ridge or rail features at the outlet port to directionally steer the liquid to the wicking pad. Surface tension forces associated with the sharp corners of the rail preferentially direct the liquid along the rail towards the wicking pad in a more controlled manner. FIG. 9 is a cross-sectional view of a fluidic cartridge 800, including a combination of a wicking pad 810 and a rail 815, in accordance with an embodiment.

Figure 10:
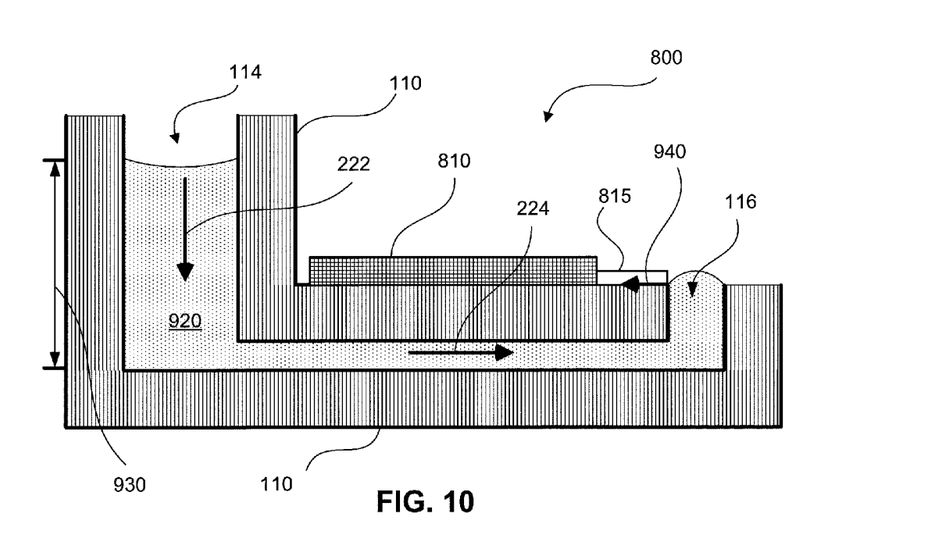
FIG. 10 shows the fluidic cartridge of FIG. 9, illustrating liquid flow within the fluidic cartridge and the effect of capillary action as the liquid is drawn along the rail.
Figure 11:
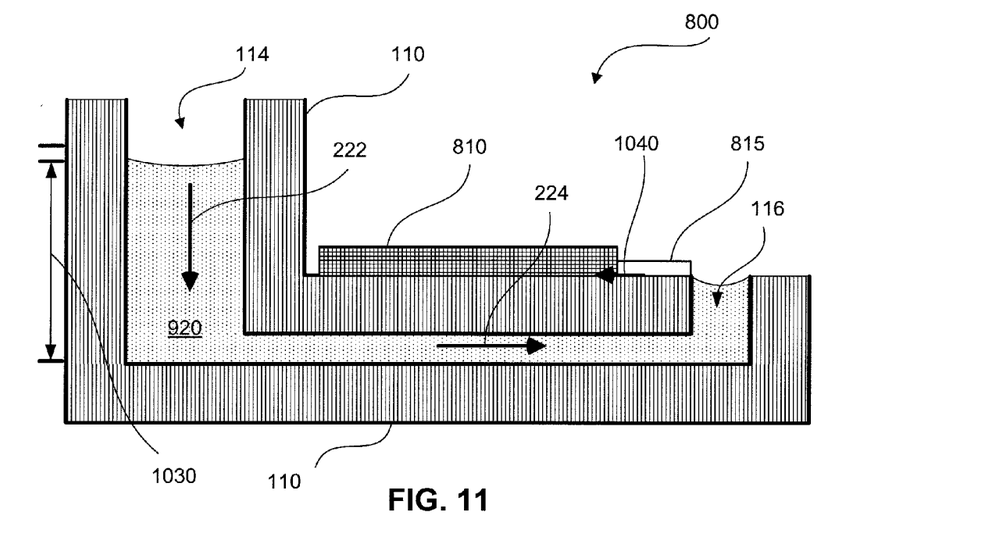
FIG. 11 shows the fluidic cartridge of FIGS. 9 and 10, illustrating the effect of capillary action as the portion of the liquid along the rail is absorbed into the wicking pad.
Figure 12:
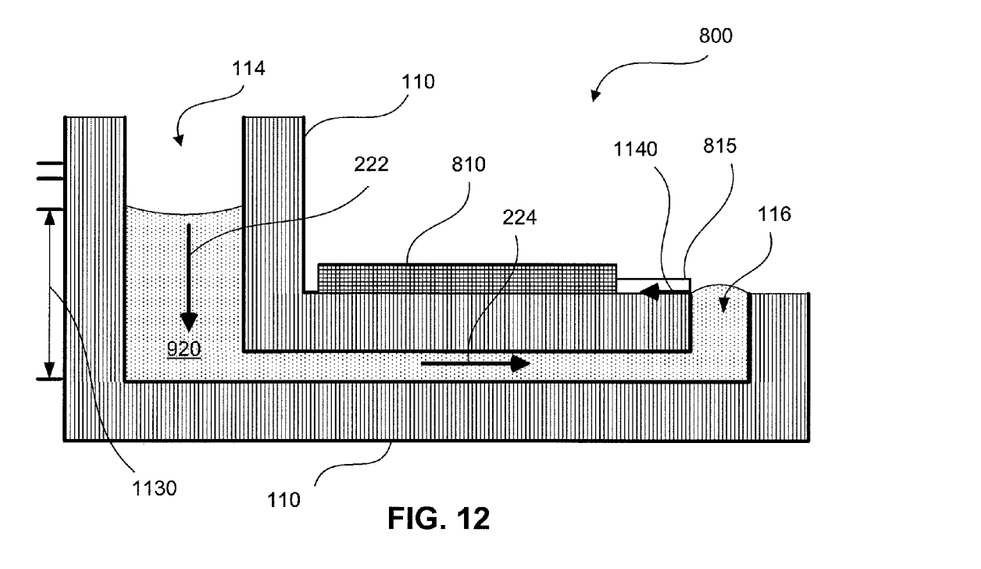
FIG. 12 shows the fluidic cartridge o FIGS. 9-11, illustrating the consequent effect of capillary action along the rail as liquid is drawn along the rail.

FIGS. 10-12 illustrate a process of liquid flow through fluidic cartridge 800, in accordance with an embodiment. FIG. 10 shows fluidic cartridge 800 with a liquid 920 inserted therein such that, initially, liquid 920 is at a first level 930 (indicated by a double-headed arrow) at inlet port 114. When liquid 920 contacts rail 815, a portion of liquid 920 is drawn along rail 815 by capillary action 940 (indicated by an arrow). Once this portion of liquid 920 reaches wicking pad 810, that portion of liquid 920 immediately in contact with rail 815 is drawn into wicking pad 810 by capillary action 1040 (indicated by an arrow), as shown in FIG. 11. Consequently, the level of liquid 920 at inlet port 114 drops incrementally to a second level 1030 (indicated by a double-headed arrow). Then, due to a combination of the pressure exerted by liquid 920 and ambient pressure, the process illustrated in FIGS. 10 and 11 is repeated, as liquid level at inlet port 114 drops to a third level 1130 (indicated by a double-headed arrow) and another portion of liquid 920 is drawn along rail 815 by capillary action (indicated by an arrow), as shown in FIG. 12.

Figure 13:
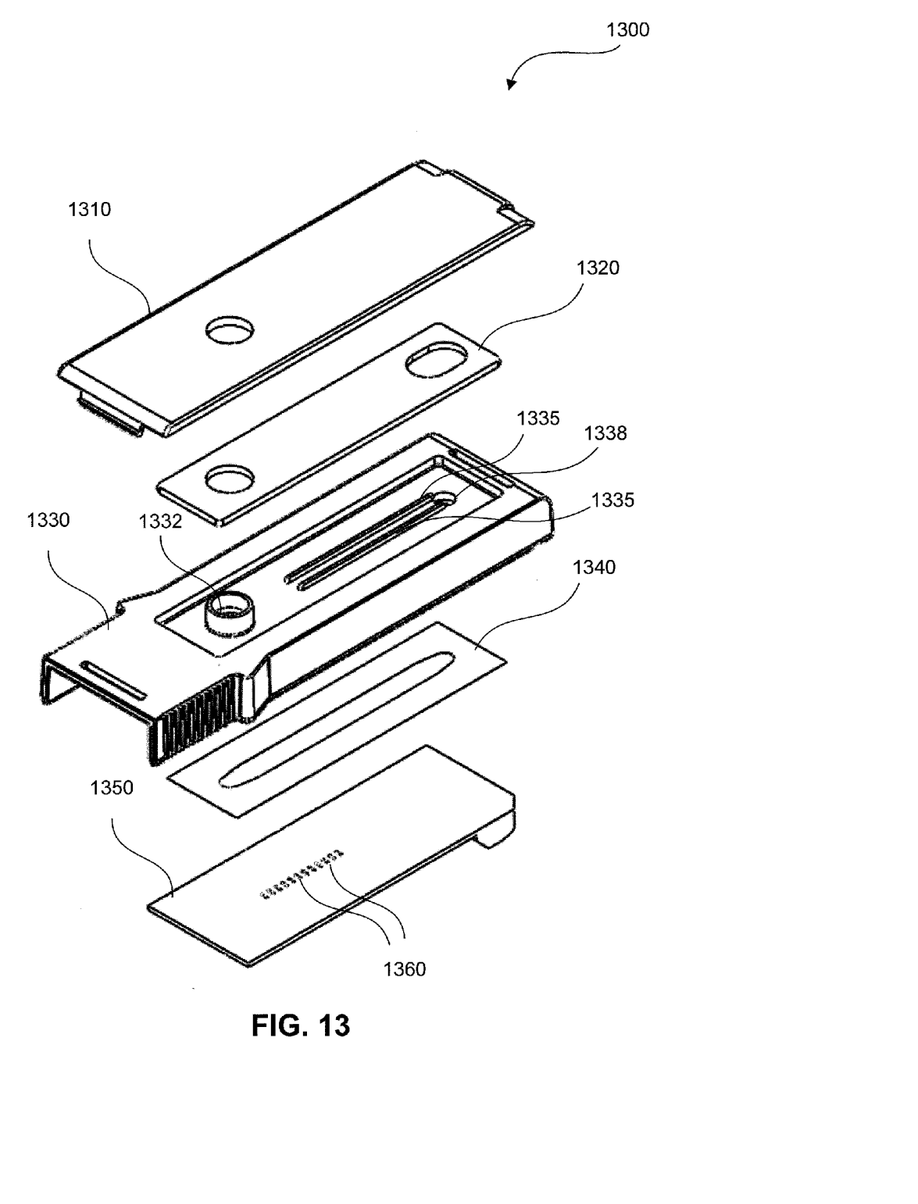
FIG. 13 shows an exploded view of an exemplary fluidic cartridge, in accordance with an embodiment.
Figure 14:
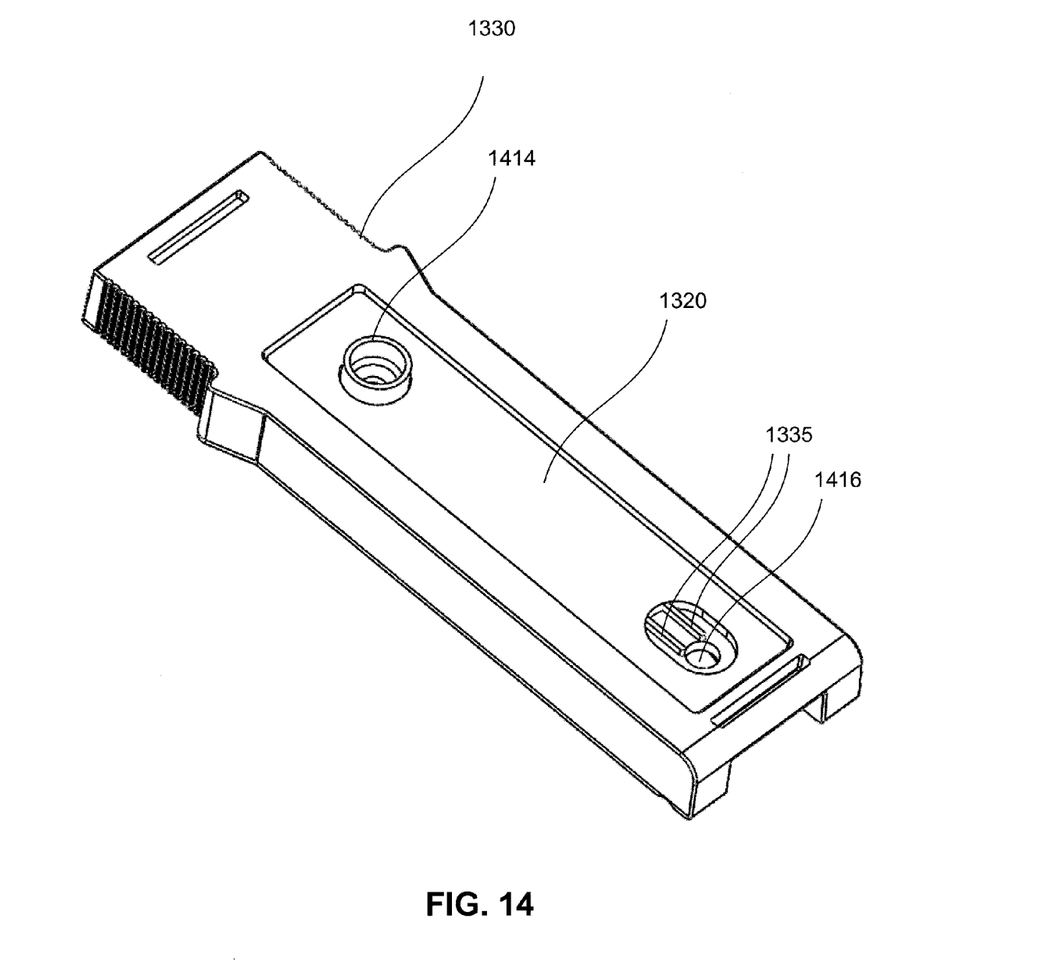
FIG. 14 shows an elevated view of a portion of the exemplary fluidic cartridge of FIG. 13, shown here to illustrate the way the upper component and wicking pad may be assembled, in accordance with an embodiment.

FIG. 13 shows an exploded view of an exemplary cartridge 1300 including a wicking pad and rails, in accordance with an embodiment. Cartridge 1300 includes a lid 1310 and a wicking pad 1320, both of which fit over an upper component 1330. Upper component 1330 defines an inlet port 1332, a pair of rails 1335, and an outlet port 1338. Upper component 1330 attached via an adhesive gasket 1340 to a planar waveguide arrangement 1350, shown here with a plurality of a microarray of protein "spots" 1360 printed thereon. FIG. 14 further shows upper component 1330 in combination with wicking pad 1320. As shown in FIG. 14, wicking pad 1320 fits around inlet port 1332 and outlet port 1338 such that combination of features function to provide the flow control mechanism described in FIGS. 9-12.

Changes may be made in the above methods and systems without departing from the scope hereof It should thus be noted that the matter contained in the above description or shown in the accompanying drawings should be interpreted as illustrative and not in a limiting sense. The following claims are intended to cover generic and specific features described herein, as well as statements of the scope of the present method and system, which, as a matter of language, might be said to fall therebetween.

Although each of the aforedescribed embodiments have been illustrated with various components having particular respective orientations, it should be understood that the system as described in the present disclosure may take on a variety of specific configurations with the various components being located in a variety of positions and mutual orientations and still remain within the spirit and scope of the present disclosure. Furthermore, suitable equivalents may be used in place of or in addition to the various components, the function and use of such substitute or additional components being held to be familiar to those skilled in the art and are therefore regarded as falling within the scope of the present disclosure. Therefore, the present examples are to be considered as illustrative and not restrictive, and the present disclosure is not to be limited to the details given herein but may be modified within the scope of the appended claims.

The invention claimed is:

1. A device for analyzing or processing a liquid sample, said device comprising a first substrate, a second substrate, a fluidic channel, an inlet port and an outlet port, said second substrate having an inner surface and an outer surface, said first substrate forming, at least in part, the lower wall of said fluidic channel, the inner surface of said second substrate forming, at least in part, the upper wall of said fluidic channel, said fluidic channel being connected to said inlet port and said outlet port, wherein said device further comprises a wicking pad being attached to the outer surface of said second substrate, said wicking pad being positioned at a distance from said outlet port, wherein said liquid sample has a top liquid surface height of h at the inlet port, said height h being defined relative to the outlet port, and relative to a level orientation.

2. The device of claim 1, wherein said distance between the wicking pad and the outlet port is sufficient to prevent said wicking pad from draining the fluidic channel.

3. The device of claim 1, wherein said distance between the wicking pad and the outlet port is sufficient to prevent liquid that has made contact with the wicking pad from flowing back into the outlet port.

4. The device of claim 1, wherein said wicking pad is made of a material having a wicking rate of between 10 and 200 seconds per 4 centimeters (cm) of said material.

5. The device of claim 1, further comprising a rail structure between the outlet port and the wicking pad for directing capillary flow from the outlet port to the wicking pad.

6. The device of claim 1, wherein said distance between the wicking pad and the outlet port is between 1 and 5 mm.

7. The device of claim 1, wherein said height h is achieved by placing said device in a rack with a pre-determined tilt angle.

8. The device of claim 1, wherein said device is designed with an internal tilt relative to a level orientation, said internal tilt being sufficient to drive flow of said liquid sample from the inlet port to the outlet port.

9. The device of claim 8, wherein said tilt is at an angle between 2 and 45 degrees relative to a level orientation.

10. The device of claim 1, wherein said first substrate comprises a planar waveguide.

11. The device of claim 10, further comprising a refractive volume for optically coupling to the planar waveguide a light beam provided by a light source.

12. The device of claim 11, wherein said refractive volume is integrally formed from the planar waveguide.

13. A device for analyzing or processing a liquid sample, said device comprising a first substrate, a second substrate, a fluidic channel, an inlet port and an outlet port, said second substrate having an inner surface and an outer surface, said first substrate forming, at least in part, the lower wall of said fluidic channel, the inner surface of said second substrate forming, at least in part, the upper wall of said fluidic channel, said fluidic channel being connected to said inlet port and said outlet port wherein said device further comprises a wicking pad being attached to the outer surface of said second substrate, said wicking pad being positioned at a distance from said outlet port, wherein said liquid sample flows through the fluidic channel from the inlet port towards the outlet port after being added to the inlet port, wherein said liquid sample forms an inlet port reservoir at the vicinity of the inlet port before flowing through the fluidic channel, said inlet port reservoir having a depth of $H_1$, $H_1$ being between 1 and 10 mm.

14. The device of claim 13, wherein the flow of said liquid sample is driven by a pressure differential between the inlet port and the outlet port.

15. The device of claim 13, wherein said wicking pad is made of a material having a wicking rate of between 10 and 200 seconds per 4 centimeters (cm) of said material.

16. The device of claim 13, further comprising a rail structure between the outlet port and the wicking pad for directing capillary flow from the outlet port to the wicking pad.

17. The device of claim 13, wherein said device is designed with an internal tilt relative to a level orientation, said internal tilt being sufficient to drive flow of said liquid sample from the inlet port to the outlet port.

18. The device of claim 13, wherein said wicking pad is made of a material having a certain absorbance rate, wherein the surface tension of the liquid sample emerging from the outlet port breaks the fluidic connection between the wicking pad and the outlet port when said absorbance rate exceeds the rate at which said liquid sample emerges from the outlet port, thereby preventing further fluidic flow from the outlet port to the wicking pad.

19. The device of claim 18, wherein said liquid flow is restored by adding liquid to the inlet port, without requiring removal of existing liquid from the device.

* * * * *